United States Patent [19]

Shima et al.

[11] 3,953,535
[45] Apr. 27, 1976

[54] PROCESS FOR THE PREPARATION OF ALKENYLBENZENES

[75] Inventors: Takeo Shima; Takanori Urasaki, both of Iwakuni; Iwao Omae, Hino, all of Japan

[73] Assignee: Teijin Limited, Osaka, Japan

[22] Filed: Dec. 9, 1974

[21] Appl. No.: 530,583

Related U.S. Application Data

[63] Continuation-in-part of Ser. No. 495,762, Aug. 8, 1974, abandoned, which is a continuation-in-part of Ser. No. 422,648, Dec. 7, 1973, abandoned.

[52] U.S. Cl. ........................ 260/668 B; 260/671 A
[51] Int. Cl.$^2$ .......................................... C07C 3/52
[58] Field of Search ................... 260/668 B, 671 A

[56] References Cited
UNITED STATES PATENTS
3,766,288   10/1973   Shima et al. ................... 260/668 B

*Primary Examiner*—Veronica O'Keefe
*Attorney, Agent, or Firm*—Donald R. Johnson; J. Edward Hess

[57] ABSTRACT

A process for preparing alkenylbenzenes, which comprises reacting an alkylbenzene with 1,3-butadiene at elevated temperature in the presence of an alkali metal catalyst in the substantial absence of oxygen and moisture, characterized in that said catalyst is composed of 1. 0.0005 to 0.03% by weight, based on the alkylbenzene, of metallic potassium, and 2. metallic sodium in an amount expressed in percent by weight, based on the alkylbenzene, determined by the following relationship (i)

$$-0.59x + 0.025 \geq \text{Na}$$

wherein $x$ is the amount expressed in percent by weight of the metallic potassium used.

7 Claims, 1 Drawing Figure

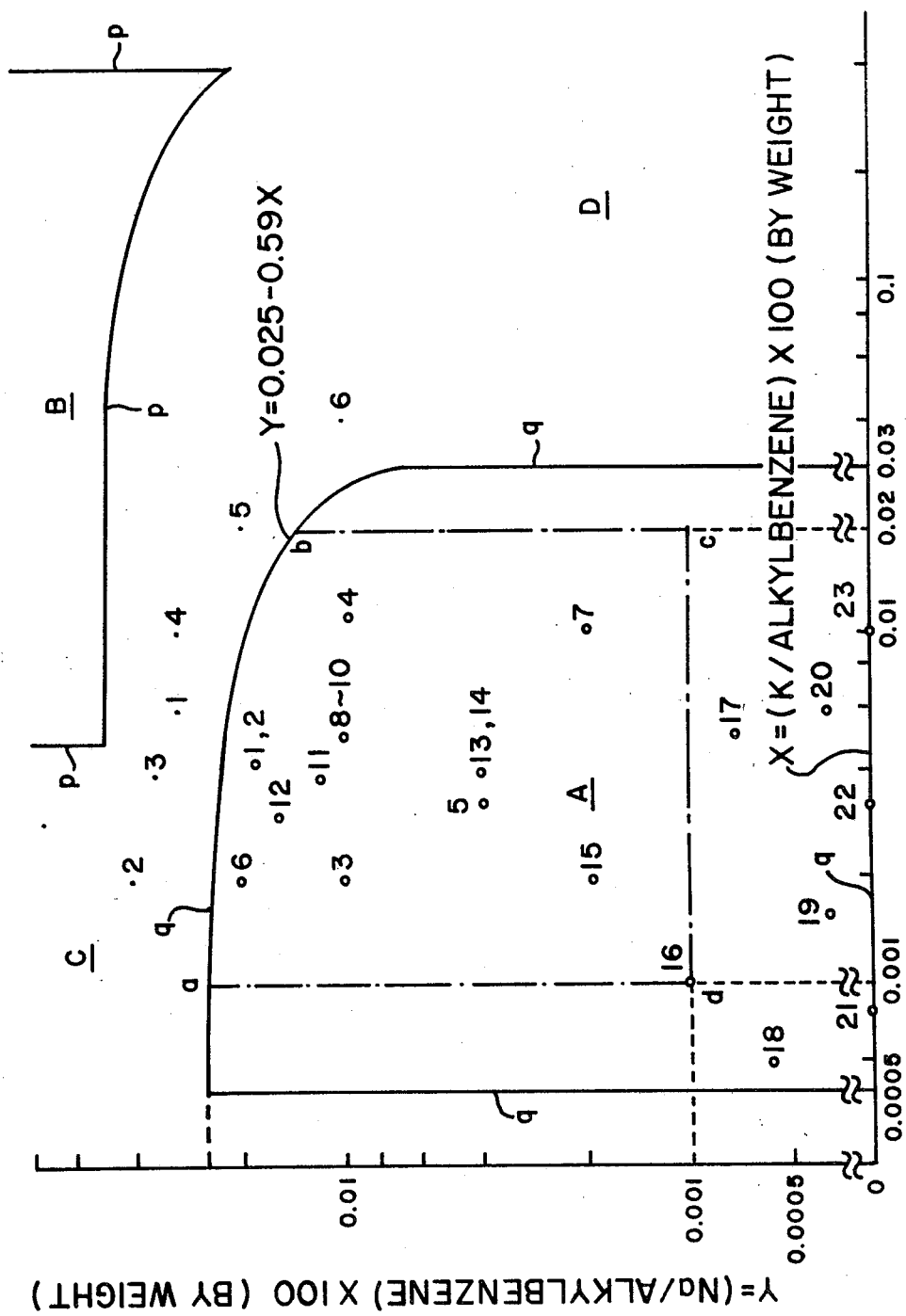

PROCESS FOR THE PREPARATION OF ALKENYLBENZENES

CROSS REFERENCE TO RELATED APPLICATION

This application is a continuation-in-part of Ser. No. 495,762, filed Aug. 8, 1974 now abandoned; which is a continuation-in-part of Ser. No. 422,648, filed Dec. 7, 1973, and now abandoned.

This invention relates to an improved process for preparing alkenylbenzenes by reacting an alkylbenzene with 1,3-butadiene in the presence of an alkali metal catalyst, the invention possessing such advantages as that not only as the catalyst used exceedingly inexpensive but also its recovery and reuse can be omitted. In addition, the formation of by-products, whose separation from the intended product involves a difficult and complicated operation, can be checked to provide the intended product in high purity with also an improvement in the yield. According to this invention, there is provided under the reaction conditions of a yield of above 70% by weight and a conversion of the alkylbenzene of at least 5% by weight a process which conjointly gives exceedingly excellent results with respect to such hereinafter-defined values as specific yield and S value, which values are respectively at least 1200 and 700, and also as to purity, which is at least 99 percent.

The alkenylbenzenes such as 5-(o-tolyl)pentene-(2) obtained by reacting an alkylbenzene such as o-xylene with 1,3-butadiene are industrially valuable compounds, because they can be converted to naphthalene dicarboxylic acids by cyclization, dehydrogenation and subsequent oxidation. The naphthalene dicarboxylic acids are useful as starting materials of polyesters.

A method has already been known to produce the alkenylbenzenes by reacting an alkylbenzene with 1,3-butadiene at an elevated temperature in the presence of an alkali metal other than lithium (see U.S. Pat. No. 3,244,758). This method, however, has the defect that where the alkenylbenzenes are desired in high yields, a great quantity of the expensive metallic potassium must be used. According to the sole Example given in this U.S. patent, a supported catalyst consisting of molten metallic potassium deposited upon finely divided $Na_2O$ is employed in an amount of about 0.57% by weight based on the alkylbenzene, but there is no mention as regards the yield of the product.

With the intent to improve on the aforementioned defect of the conventional method, we previously proposed a process for the preparation of alkenylbenzene (Ser. No. 238,584, now U.S. Pat. No. 3,766,288 ), which comprises reacting an alkylbenzene with 1,3-butadiene at an elevated temperature in the presence of an alkali metal catalyst in the substantial absence of oxygen and moisture, wherein said catalyst is composed of 1'. 0.005 to 0.4% by weight, based on the alkylbenzene, of metallic potassium, and 2'. metallic sodium in an amount expressed in percent by weight, based on the alkylbenzene, determined by the following relationship $$(4.1x + 2.0) \geq Na \geq (-0.073x + 0.05)$$

wherein $x$ is the amount in percent by weight of the metallic potassium that is used in (1'), above.

As a result of further researches by us, we found that a still greater improvement could be achieved by using a catalyst of a composition that could be clearly distinguished from that of the above previous proposal. That is to say, it was found that a still greater improvement could be obtained by the use of a catalyst composed of 1. 0.005 to 0.03% by weight, based on the alkylbenzene, of metallic potassium, and 2. metallic sodium in an amount expressed in percent by weight, based on the alkylbenzene, determined by the following relationship $$-0.59x + 0.025 \geq Na \qquad (i)$$

wherein $x$ is the amount in percent by weight of the metallic potassium that is used in (1), above.

According to the present invention, the amount used of the catalyst can be reduced still further from that used in the previous proposal, and moreover the yield of the intended monoalkenylbenzene is high. Hence, the cost of the catalyst is reduced still further. And especially, since the use of the higher cost metallic potassium can be reduced to a greater extent, it becomes possible to obtain the intended product in good yield with the use of an exceedingly inexpensive catalyst. Particularly, as shown by the hereinafter given examples that have been presented along with control experiments, a process can be provided which conjointly gives excellent results in that the specific yield is above 1200 and the S value is above 700, while the product purity is at least 99 percent.

Further, according to our researches, in this reaction wherein the reaction system is one using an alkali metal catalyst the amount of catalyst actually consumed, i.e., the amount of the alkali metal compound dissolved and the fine alkali metal and alkali metal compound remaining without being substantially separated from the reaction product system, was found to be proportionate to the amount of the catalyst used in the reaction. Hence, in the case where the catalyst must be used in a large amount, it becomes necessary from the standpoint of the manufacturing cost of the intended product that the catalyst be separated and recovered from the reaction product system and be reused, insofar as possible. Since in accordance with the invention process a high yield can be achieved by using a catalyst of lesser cost in a lesser amount, it becomes possible by a suitable choice of such conditions as the reaction temperature and the rate at which the butadiene is introduced to the reaction system to do away with the need for the step of separating, recovering and reusing the catalyst. Thus, the process is freed from this troublesome operation. Again, even in the case where the separation, recovery and reuse of the catalyst are performed, the amount consumed of the catalyst can be reduced, since only a smaller amount needs to be used in the first place.

Further, the formation of by-products that are difficult to separate from the intended product are checked according to the invention process. For instance, when the product obtained by the reaction of o-xylene and 1,3-butadiene is submitted to a cyclization reaction to convert it to 1,5-dimethyltetralin, the by-products such as 5-(o-tolyl)pentene-(3) or 5-(o-tolyl)pentene-(4) are difficult to convert to 1,5-dimethyltetralin and a major portion of the by-products reacts with the once formed 1,5-dimethyltetralin to form undesirable high-boiling by-products. However, the formation of these by-products is reduced in the case of the invention process. Thus, it is not only possible to obtain the intended product of high purity but also 1,5-dimethyltetralin in better yield and higher purity, when the product is submitted to the cyclization reaction.

Accordingly, an object of this invention is to provide a much more improved process for preparing the alkenylbenzenes in much higher yields and much higher purity, as well as at much lower cost, using a catalyst composition which is much less expensive and in which the step of its recovery from the reaction product can be omitted.

Many other objects and advantages of this invention will become apparent for the following description.

The catalyst used in the process of this invention is a catalyst system composed of 1. 0.0005 to 0.03% by weight, and preferably 0.001 to 0.02% by weight, based on the alkylbenzene, of metallic potassium, and 2. metallic sodium in an amount expressed in percent by weight, based on the alkylbenzene, determined by the following relationship $$-0.59x + 0.025 \geq \text{Na} \qquad (i)$$

wherein $x$ is the amount in percent weight of the metallic potassium used.

The limits of the composition of the alkali metal catalyst in our hereinabove-noted previous proposal and those in the case of the present invention are shown in the FIGURE. In the FIGURE, which is a logarithmic graph, the percent by weight of metallic potassium based on the alkylbenzene is plotted as abscissa and the percent by weight of metallic sodium is plotted as ordinate. In the FIGURE, the area B enclosed by line $p$ indicates the limit of the content of the alkali metal catalyst in the composition that was previously proposed by us, while the area A enclosed by line $q$ indicates the limit of the content of the alkali metal catalyst used in the composition of the present invention. And in the FIGURE, the area enclosed by the curved line $ab$, the dot-and-dash line $bc$, the dot-and-dash line $cd$ and the dot-and-dash line $da$ define the range of the composition of the alkali metal catalyst that is preferably used in this invention.

If metallic potassium is used in an amount in excess of that specified above and is of an amount without the area of the invention and within the area indicated by D in FIGURE, it not only results in increased cost of the catalyst and the product but also results in increasing the formation of objectionable by-products, which are difficult to separate from the intended product, and get into trouble during the performance of the cyclization reaction. Also, the hereinafter-defined specific yield becomes poorer. Furthermore, such excessive amounts cause disadvantages in respect of the handling of the catalyst, the operation of the reaction and the safety of the reaction equipment. In addition, there arises the necessity of separating and recovering the catalyst from the reaction product. On the other hand, if the amount of metallic potassium is below the lower limit of the above-specified range, the product cannot be obtained in good yield even if the amount of metallic sodium is increased. If the amount of metallic sodium is larger beyond the above-specified range and within the area shown by C in the FIGURE, the specific yield becomes poor, and the amounts of undesirable by-products increase as in the area D mentioned above. In the FIGURE, the marks o and . denote the hereinafter given examples and control experiments, and the numbers appended thereto indicate the corresponding examples or control experiments.

The present invention embraces a case where metallic potassium is used singly as the catalyst, or where it is used cojointly with metallic sodium as the catalyst. In the latter case, they can be added to the reaction system separately but they are desirably added in the form of an alloy, said alloy functioning as the catalyst. Where the catalyst composed of metallic potassium and metallic sodium is used in the form of an alloy, these metals are mixed in the molten state in the absence of oxygen and moisture, as is well known. The absence of oxygen and moisture can be provided, as by purging the space in which the mixture is contained with a dry, inert gas such as nitrogen or argon. Alternately, these metals can be shut off from oxygen by immersing them in a solvent such as xylene, benzene, toluene or heptane. The alloy can also be obtained, as is well known, by heating metallic sodium and a potassium compound such as potassium oxide, potassium carbonate, potassium hydroxide or a potassium halide in the absence of oxygen and moisture. The catalyst, if desired, can be used supported on a suitable carrier. Usable as the carrier are such materials as graphite, $Na_2O$, $K_2O$, $CaO$, $MgO$, $BaO$, $NaCl$, $KF$, $KCl$, $KBr$, $Na_2CO_3$, $K_2CO_3$, silica, alumina and iron.

Except that the above-described catalyst system is used, the process of the present invention can be carried out as in our previous proposal by reacting alkylbenzenes with 1,3-butadiene in the substantial absence of oxygen and moisture at an elevated temperature.

The starting alkylbenzenes that are useful in the present invention are those compounds in which at least one alkyl group having 1 to 2 carbon atoms is attached to the benzene ring and can be expressed, for example, by the following formula

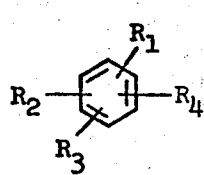

wherein $R_1$ is an alkyl group having 1 or 2 carbon atoms, and $R_2$, $R_3$ and $R_4$, which may be the same or different, is hydrogen or an alkyl group of 1 to 3 carbon atoms. Preferred alkylbenzenes are toluene, xylene, ethylbenzene, trimethylbenzene and tetramethylbenzene.

Usually, the reaction is carried out at 90° to 200°C, preferably 100°C to 190°C, and more preferably 110°C to 180°C. The mole ratio of 1,3-butadiene to the alkylbenzene can be optionally chosen from those already known. For example, the mole ratio of the alkylbenzene to 1,3-butadiene is 1:0.001 to 0.4, preferably 1:0.01 to 0.3, and more preferably 1:0.05 to 0.2. The reaction can be performed either continuously or batchwise. In the continuous method, a multiplicity of reaction zones may be provided. A reaction time or residence time of 1/20 to 10 hours, and preferably about 1/6 to 8 hours may usually be employed.

The reaction is preferably carried out at boiling conditions in a staged reactor with the vapor (alkylbenzene) from the stages other than the first being recycled to the first stage and with an alkylbenzene (makeup plus recycle): 1,3-butadiene weight ratio of 15:1 to 25:1. This procedure has several advantages. Since the reaction is exothermic use of boiling conditions effects removal of the heat of reaction and thus provides a ready means of temperature control. Additionally, recycling the vapor to the first stage effects a small but important yield increase which it should be noted is obtained without additional investment. In other words since the vapor is obtained as a result of reaction temperature control it is available for recycle "free" in that no additional energy is required. This is not the case with the recycled alkylbenzene obtained by fractionating the reaction product externally of the reaction zones.

In the staged reactor system and with the alkylbenzene:butadiene ratio of 15:1 to 25:1 the reaction mixture will boil between about 145°C and 155°C at one atmosphere. It varies because the composition of the reaction mixture varies between stages and it will, of course, also vary with pressure.

The multistage reactor can be a plurality of separate reactors but is preferably one reactor divided by baffles into a plurality of reaction zones in which reactants overflow from one zone to the next.

Any of the following methods of reaction may be employed. That is, the batch method in which the reaction is carried out by concurrently charging the starting alkylbenzene, 1,3-butadiene and the catalyst from the outset; or the semibatch method in which the alkylbenzene and the catalyst are first charged, and thereafter the 1,3-butadiene is introduced incrementally with the passage of the reaction time; or the continuous method wherein the alkylbenzene, 1,3-butadiene and the catalyst are continuously introduced to the reactor. Further, these methods may also be suitably combined. However, of these methods, the semi-batch or the continuous method is to be preferred. In the case of the continuous reaction method, either the plug flow, column type of backmix flow reactor will do. The preferred method in the case of the continuous method is the so-called cross-flow reaction method which comprises providing a plurality of reaction zones, conducting the reaction liquid from the initial reaction successively to the final reaction zones while introducing the 1,3-butadiene incrementally in prescribed amounts to the several reaction zones.

No particular restriction is imposed on the reaction operation, the only requirement being that sufficient contact is had between the alkylbenzene and the 1,3-butadiene in the presence of the catalyst. However, since a resinous or gummy substance, presumably a polymer of 1,3-butadiene, adheres to the inlet for the 1,3-butadiene and tends to block the inlet, it is preferred that instead of introducing 1,3-butadiene alone into the alkylbenzene in which the catalyst is present, a mixture of 1,3-butadiene and the alkylbenzene, for example, a liquid mixture of 1,3-butadiene and alkylbenzene or a liquidgaseous mixture of 1,3-butadiene and alkylbenzene be introduced therein. Alternatively, 1,3-butadiene is fed into a space in the reaction zone and allowed to be absorbed and reacted with the surface of the alkylbenzene liquid in which the catalyst is present thereby to prevent blockage of the inlet.

After completion of the reaction, the catalyst, by-products and unreacted reactants can be removed, if necessary. While it is not particularly necessary to remove the catalyst in this invention, the catalyst can be separated from the reaction product by any known method, as by the liquid-liquid separation technique and subsequent separation of the separated lower layer, or by separating the solid phase from the liquidsolid mixture at a lower temperature, say, by filtration or centrifugation.

The following examples and control experiments will now be given for more fully illustrating the present invention. In the examples and controls, the specific yields, the S value and the recovery ratio of the catalyst after the reaction were determined in the following manner.

Specific Yield $$\text{Specific yield (S.Y.)} = \frac{\text{Yield of the product (weight)}}{\text{Amount of the catalyst metals consumed (weight)}}$$

Smaller S. Y. values denote poorer yields of the product, while greater S. Y. values denote larger yields of the product, taking economy also into consideration.

The amount of the catalyst metals consumed is measured and calculated as follows:

1. After completion of the reaction and while continuing the stirring of the reaction mixture liquid, a prescribed amount thereof is sampled. Ethyl alcohol is added to the sampled liquid (A grams) at room temperature in an amount of 20% by weight of the sampled liquid. The amount of hydrogen gas evolved (B cubic centimeters) at 20°C and 1 atm. is then measured.

The amount of the metal catalyst (mol/grams of the reaction mixture liquid) is then calculated from the measured value as follows:

$$\text{Amount of metal catalyst} = \frac{B \times \frac{273}{293} \times \frac{1}{22400} \times 2}{A}$$

2. About 0.5 gram of the metal catalyst is sampled from the reaction product liquid, after which 20 cc of ethyl alcohol is added thereto to set up a reaction. The reaction liquid is then analyzed by atomic absorption analysis, and the ratio of sodium to potassium is determined.

From the results obtained in (1) and (2), above, the amounts C (grams per gram of the reaction product liquid) of metallic sodium and potassium in the reaction product are calculated.

3. The amounts D of metallic potassium and metallic sodium added newly to the reaction system are theoretically determined as the amounts in grams of the catalyst metals per gram of the reaction product.

4. From the above results, the amounts E of catalyst metals consumed are determined by the following equation:

$$E = D - C$$

Yield and Purity

After filtering the total reaction mixture at room temperature, about 500 grams thereof is distilled with a Widmer rectifier under a reduced pressure of 22 mm Hg abs. to separate a fraction of below 75°C (rectifying column top temperature), a 75° to 170°C fraction and a residue. The 75° to 170°C fraction is collected as an alkenylated product. This alkenylated product fraction is analyzed by gas chromatography to obtain the content (percent by weight) of 5-arylpentene-(2) and 5-arylpentene-(1) or the content (percent by weight) of 5-arylhexene-(2) and 5-arylhexene-(1), and the yield of the monoalkenylated product is calculated. The unreacted alkylbenzene is contained in this alkenylated product fraction in only an amount of below 1% by weight. Further, 20 grams of the aforementioned alkenylated product fraction is submitted to distillation under the conditions of reduced pressure of 22 mm Hg abs. and reflux ratio of 20, using an Oldershaw-type rectification apparatus to obtain 10 grams of an initial fraction containing a large quantity of the intended product followed by obtaining 2 grams of a main fraction. This main fraction is analyzed by gas chromatography to determine the content (percent by weight) of 5-arylpentene-(2) and 5-arylpentene-(1) or the content (percent by weight) of 5-arylhexene(2) or 5-arylhexene-(1), which is designated the purity.

Yield

The yield is determined in the following manner from the yield of the intended product obtained as described above and the amount of 1,3-butadiene used in the reaction.

$$\text{Yield (\%)} = \frac{\text{Yield of intended product (g)}}{\text{1,3-butadiene used (g)}} \times \frac{54}{\text{Molecular weight of intended product}} \times 100$$

S Value

The S value is indicated by the ratio of the yield (g) of the intended product resulting from the reaction to the sum total of the weights of potassium and sodium present in the reaction system. In this case, the yield (g) of the intended product is meant the yield per batch in the semi-batch reaction, while in the continuous reaction it is meant the yield (g) of the intended product formed per average residence time. The greater the S value, the smaller the amount used of the catalyst per unit of the monoalkenylated product formed, thereby making it possible to discard the catalyst without the necessity of recovering the catalyst and reusing it. On the other hand, the smaller the S value, the greater the amount used of the catalyst per unit of the monoalkenylated product formed, thus making it necessary to reuse the catalyst because of economic considerations.

EXAMPLES 1 – 7 and 8 – 10 and CONTROLS 1 – 6

In a stream of dry nitrogen ($O_2$ content 1 ppm, moisture content 0.5 ppm by weight), metallic sodium (Na purity 99.92%, potassium content 250 ppm) in an amount of 1.08 grams (0.018 wt. % based on the starting xylene) and metallic potassium (K purity 99.1%, sodium content 1.0%) in an amount of 0.25 gram (0.0042 wt. % based on the starting xylene) were melt-blended to prepare an alloy, to which was then added 6000 grams of substantially anhydrous o-xylene which had been obtained by heating under reflux in the presence of metallic potassium and subsequent evaporation and distillation. After heating this mixture with stirring for one hour at 130°C in an atmosphere of the above-specified nitrogen, 400 grams of 1,3-butadiene was introduced during a period of 2 hours to carry out the reaction. After completion of the reaction and while stirring the reaction mixture, sample thereof was taken for determining the catalyst consumed. After cooling the reaction mixture liquid immediately to 110°C and while holding it at this temperature, the stirring was stopped and the reaction mixture liquid was allowed to stand still for 30 minutes, whereupon it separated into the catalyst and the intended product phase. The intended product phase was then distilled under reduced pressure conditions of 22 mm Hg abs. to collect a 112° to 122°C fraction, thus obtaining the intended 5-(o-tolyl)pentene-(2). The yield, inclusive of the aforementioned sample, was 1,046 grams.

Results obtained by operating the experiment in the same manner as described hereinabove but varying the amounts of the metallic potassium and sodium, the class of alkylbenzene, the reaction temperature and the reaction time are shown in Table 1, along with the results of the foregoing Example 1. Examples 4 and 5 were conducted under boiling conditions whereas Examples 1 to 3 and 7 were not.

Table 1

| NO. | Starting material | Catalyst composition based on alkylbenzene | | | Reaction temperature (°C) | Reaction time (hr) | Intended product | | | | | S-value |
|---|---|---|---|---|---|---|---|---|---|---|---|---|
| | | Na (wt.%) | K (wt.%) | Total (wt.%) | | | Name | Yield (gr) | Rate of yield (%) | Purity (%) | Specific yield | |
| Ex. 1 | O-xylene | 0.018 | 0.0042 | 0.0222 | 130 | 2.0 | 5-(o-tolyl)pentene-(2) | 1046 | 84.9 | 99.0 | 1410 | 763 |
| Ex. 2 | P-xylene | 0.018 | 0.0042 | 0.0222 | 130 | 2.0 | 5-(p-tolyl)pentene-(2) | 1046 | 84.9 | 99.1 | 1345 | 763 |
| Ex. 3 | O-xylene | 0.010 | 0.0020 | 0.0120 | 144 | 1.5 | 5-(o-tolyl)pentene-(2) | 1017 | 83.5 | 99.3 | 1542 | 1385 |
| Ex. 4 | O-xylene | 0.0098 | 0.0110 | 0.0208 | 144 | 1.5 | " | 1056 | 86.0 | 99.3 | 1205 | 822 |
| Ex. 5 | " | 0.0040 | 0.0033 | 0.0073 | 170 | 1.0 | " | 1027 | 83.3 | 99.0 | 2835 | 2279 |
| Ex. 6 | " | 0.020 | 0.002 | 0.022 | 130 | 2.0 | " | 1044 | 85.1 | 99.4 | 1813 | 853 |
| Ex. 7 | " | 0.002 | 0.010 | 0.012 | 130 | 2.0 | " | 1048 | 85.7 | 99.0 | 2179 | 1424 |
| Control 1 | O-xylene | 0.030 | 0.006 | 0.036 | 130 | 2.0 | 5-(o-tolyl)pentene-(2) | 1015 | 83.7 | 99.0 | 965 | 459 |
| " 2 | " | 0.040 | 0.002 | 0.042 | 130 | 2.0 | " | 989 | 80.5 | 99.3 | 1344 | 389 |
| " 3 | " | 0.035 | 0.004 | 0.039 | 130 | 2.0 | " | 1011 | 81.9 | 98.9 | 1053 | 427 |
| " 4 | " | 0.030 | 0.010 | 0.040 | 130 | 2.0 | " | 1005 | 81.3 | 98.7 | 840 | 413 |
| " 5 | " | 0.020 | 0.020 | 0.040 | 130 | 2.0 | " | 989 | 79.7 | 98.3 | 788 | 399 |
| " 6 | " | 0.010 | 0.040 | 0.050 | 130 | 2.0 | " | 998 | 80.5 | 98.5 | 650 | 323 |
| Ex. 8 | m-xylene | 0.010 | 0.005 | 0.015 | 140 | 2.0 | 5-(m-tolyl) | 983 | 83.3 | 99.5 | 1825 | 1103 |

Table 1-continued

| NO. | Starting material | Catalyst composition based on alkylbenzene | | | Reaction temperature (°C) | Reaction time (hr) | Intended product | | | | Specific yield | S-value |
| --- | --- | --- | --- | --- | --- | --- | --- | --- | --- | --- | --- | --- |
| | | Na (wt.%) | K (wt.%) | Total (wt.%) | | | Name | Yield (gr) | Rate of yield (%) | Purity (%) | | |
| Ex. 9 | Toluene | 0.010 | 0.005 | 0.015 | 130 | 2.0 | pentene-(2) 5-phenyl-pentene-(2) | 974 | 79.5 | 99.2 | 1448 | 1051 |
| Ex. 10 | Ethyl-benzene | 0.010 | 0.005 | 0.015 | 140 | 2.0 | 2-phenyl-hexene-(2) | 1013 | 82.9 | 99.5 | 1301 | 1103 |

EXAMPLE 11

A 70-liter stirred continuous reaction vessel was charged with 40 Kg of substantially anhydrous o-xylene and an alloy consisting of 8.0 grams of metallic sodium and 2.40 grams of metallic potassium. The temperature of the reaction vessel was raised to 130°C, and the mixture was stirred for one hour. Dehydrated 1,3-butadiene and dehydrated o-xylene were then introduced from the inlet at the bottom of the reaction vessel at the rate of 1.25 Kg per hour and 19 Kg per hour, respectively, to initiate the reaction.

The reaction product was withdrawn at a prescribed rate via a pipe inserted in the central part of the reaction vessel, while ensuring that about 45 Kg of the product always remains present in the reaction vessel. The withdrawal of the reaction product liquid was performed by means of a decanter of 10-liter capacity connected to the reaction vessel. The reaction liquid was transferred to the decanter, and the supernatant liquid was withdrawn by this decanter. The catalyst separated by the decanter was continuously returned to the reaction vessel.

On the other hand, a suspension of finely dispersed alloy consisting of 2.25 grams of sodium and 0.75 gram of potassium per kilogram of o-xylene was fed to the reaction vessel at a rate of one kilogram per hour. The process was operated by this procedure for 10 days. The supernatant liquid withdrawn was distilled at a reduced pressure of 22 mm Hg abs., and a fraction boiling at 115°C to 125°C was extracted at a rate of 2.88 Kg per hour.

| Specific yield | 1210 |
| --- | --- |
| S value | 917 |
| Purity | 99.0% |
| Yield | 74.3% |

EXAMPLE 12

The same reactor as that used in Example 11 was used, except that the reaction mixture was withdrawn externally of the system directly without decantation. This reactor was charged with 40 Kg of dehydrated o-xylene and 8.10 grams of an alloy consisting of 6.75 grams of metallic sodium and 1.35 grams of metallic potassium, after which the inside temperature of the reactor was raised to 140°C, and heating was continued for one hour with stirring. The reaction was then carried out for 30 minutes by blowing dehydrated 1,3-butadiene in at the rate of 1.25 Kg per hour. This was followed by introducing dehydrated o-xylene and dehydrated 1,3-butadiene into the reactor at the rates of respectively 19 Kg and 1.25 Kg per hour. On the other hand, a suspension of finely dispersed alloy in an amount of 3.6 grams consisting of metallic sodium and metallic potassium in a weight ratio of 5:1 was fed as catalyst to the reactor at the rate of one kilogram per hour for each kilogram of the o-xylene. The process was operated by the foregoing procedure for 2 days.

The reaction liquid was fed to a separately provided 10-liter decanter. After having withdrawn from the bottom of the decanter a liquid containing the used catalyst at the rate of 30 grams per hour, the clear liquid remaining at the upper part of the decanter was withdrawn. The so-obtained clear liquid was then vacuum distilled under reduced pressure of 22 mmHg abs. to obtain a fraction boiling at 115° to 125°C at the rate of 2.99 Kg per hour.

| Specific yield | 1217 |
| --- | --- |
| S value | 794 |
| Purity | 99.5% |
| Yield | 77.2% |

EXAMPLE 13

A continuous reaction tank made by coupling in series five stirrer-equipped tanks, each of 500 ml capacity (effective liquid charging capacity of 300 ml), and adapted that the liquid of the first tank flows into the second tank via an overflow line, after which the liquid flows in like manner successively from the second through the fifth tanks to be finally withdrawn therefrom was employed. To the first tank of this series of reaction tanks was fed dehydrated o-xylene continuously at the rate of 600 grams per hour. The inside temperature of the several tanks was then raised to 130°C, and the speed of the stirrers was adjusted at 600 rpm, after which an alloy consisting of metallic sodium and metallic potassium in a weight ratio of 1:1 was fed to the first tank at the rate of 48 mg per hour with a microfeeder. After the lapse of one hour after initiating the feed of the o-xylene and the catalyst, dehydrated 1,3-butadiene was introduced continuously at the rate of 8 grams per hour to each of the tanks, thus carrying out the reaction by the introduction of a total of 40 grams per hour of the 1,3-butadiene. The reaction liquid was continuously withdrawn into a 1-liter flask from the fifth tank as a result of its being overflowed therefrom. The inside temperature of this flask was held at 110°C, and the catalyst was separated. The catalyst phase was withdrawn from the bottom part of the flask intermittently at the rate of one gram per hour, while 637 grams per hour of a clear liquid was obtained from the upper part of the flask. This clear liquid was submitted to vacuum distillation under reduced pressure of 22 mm Hg abs. to obtain a fraction boiling at 115° to 125°C at the rate of 101 grams per hour.

|   |   |
|---|---|
| Specific yield | 5402 |
| S value | 2104 |
| Purity | 99.5% |
| Yield | 85.2% |

EXAMPLE 14

The reaction was carried out in the same way as in Example 13 except that the reaction was performed under atmospheric boiling conditions at 144° to 148°C and the evaporated vapor from each reaction tank was condensed and then all fed back to the first tank.

The results are shown in the following table:

|   |   |
|---|---|
| Specific yield | 5497 |
| S value | 2104 |
| Purity | 99.5% |
| Yield | 86.7% |

EXAMPLES 15 to 23

The reaction was carried out in the same way as in Example 1 except that the kinds and amounts of the catalysts, the reaction temperature and period were varied as indicated in Table 2.

The results are shown in Table 2.

Table 2

| No. | Starting material | Catalyst composition based on alkylbenzene | | | Reaction temperature (°C) | Reaction time (hr) | Intended product | | | | | |
|---|---|---|---|---|---|---|---|---|---|---|---|---|
|   |   | Na (wt.%) | K (wt.%) | Total (wt.%) |   |   | Name | Yield (gr) | Rate of yield (%) | Purity (%) | Specific yield | S-value |
| Ex. 15 | O-xylene | 0.002 | 0.002 | 0.004 | 144 | 2.0 | 5-(o-tolyl) pentene-(2) | 1019 | 82.8 | 99.3 | 5750 | 4170 |
| Ex. 16 | O-xylene | 0.001 | 0.001 | 0.002 | 144 | 2.0 | " | 1018 | 82.7 | 99.3 | 10420 | 8340 |
| Ex. 17 | O-xylene | 0.00075 | 0.005 | 0.00575 | 144 | 2.0 | " | 1018 | 82.7 | 99.3 | 3630 | 2900 |
| Ex. 18 | O-xylene | 0.006 | 0.0006 | 0.0012 | 144 | 2.0 | " | 1016 | 82.5 | 99.5 | 15400 | 13900 |
| Ex. 19 | " | 0.0004 | 0.0015 | 0.0019 | 144 | 2.0 | " | 1004 | 81.6 | 99.4 | 10800 | 8680 |
| Ex. 20 | " | 0.0004 | 0.006 | 0.0064 | 144 | 2.0 | " | 1003 | 81.5 | 99.4 | 3450 | 2570 |
| Ex. 21 | " | 0 | 0.0008 | 0.0008 | 144 | 2.0 | " | 995 | 80.8 | 99.4 | 21500 | 20400 |
| Ex. 22 | " | 0 | 0.003 | 0.003 | 144 | 2.0 | " | 997 | 81.0 | 99.4 | 6810 | 5460 |
| Ex. 23 | " | 0 | 0.01 | 0.01 | 144 | 2.0 | " | 1000 | 81.2 | 99.0 | 2780 | 1640 |

The invention claimed is:

1. A process for preparing alkenylbenzenes, which comprises reacting an alkylbenzene with 1,3-butadiene at an elevated temperature in the presence of an alkali metal catalyst in the substantial absence of oxygen and moisture, characterized in that said catalyst is composed of
   1. 0.0005 to 0.03% by weight, based on the alkylbenzene, of metallic potassium, and
   2. metallic sodium in an amount expressed in percent by weight, based on the alkylbenzene, determined by the following relationship (i)

$$-0.59x + 0.025 \geq Na \qquad (i)$$

wherein $x$ is the amount expressed in percent by weight of the metallic potassium used.

2. The process of claim 1 wherein the amount of the metallic potassium is 0.001 to 0.02% by weight based on the alkylbenzene.

3. The process of claim 1 wherein the amount of the metallic sodium, expressed in percent by weight, is as determined by the following relationship (1')

$$-0.59x + 0.025 \geq Na \geq 0.001 \qquad (1')$$

wherein $x$ is as above defined.

4. The process of claim 1 wherein said reaction is carried out at 90°C to 200°C.

5. The process of claim 1 wherein the mol ratio of said alkylbenzene to 1,3-butadiene is 1:0.001 to 0.4.

6. The process of claim 4 carried out in a multiplicity of reaction zones under boiling conditions and alkylbenzene vapor generated thereby is recycled to the first reaction zone.

7. The process of claim 1 carried out in a multiplicity of reaction zones under boiling conditions and alkylbenzene vapor generated thereby is recycled to the first reaction zone.

* * * * *